United States Patent
Fripp et al.

(10) Patent No.: US 11,385,152 B2
(45) Date of Patent: Jul. 12, 2022

(54) USING FLUIDIC DEVICES TO ESTIMATE CUT OF WELLBORE FLUIDS

(71) Applicant: Halliburton Energy Services, Inc., Houston, TX (US)

(72) Inventors: Michael L. Fripp, Carrollton, TX (US); Maxime P M Coffin, Frisco, TX (US); Thomas J. Frosell, Irving, TX (US); Larry S. Eoff, Porter, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/630,978

(22) PCT Filed: Dec. 7, 2017

(86) PCT No.: PCT/US2017/065188
§ 371 (c)(1),
(2) Date: Jan. 14, 2020

(87) PCT Pub. No.: WO2019/112597
PCT Pub. Date: Jun. 13, 2019

(65) Prior Publication Data
US 2020/0300740 A1     Sep. 24, 2020

(51) Int. Cl.
*E21B 47/06*     (2012.01)
*G01N 11/08*     (2006.01)
(Continued)

(52) U.S. Cl.
CPC .............. *G01N 11/08* (2013.01); *E21B 43/12* (2013.01); *E21B 47/06* (2013.01); *E21B 49/0875* (2020.05); *G01N 33/2823* (2013.01)

(58) Field of Classification Search
CPC ...... E21B 49/0875; E21B 47/06; E21B 43/12; G01N 33/2823
See application file for complete search history.

(56) References Cited

U.S. PATENT DOCUMENTS 8,584,762 B2    11/2013   Fripp et al.
8,739,869 B2 *   6/2014   Willingham ............. C09K 8/58
                                            166/272.6

(Continued)

FOREIGN PATENT DOCUMENTS

WO    WO 2018/063149 A1    4/2018

OTHER PUBLICATIONS

International Search Report and The Written Opinion of the International Search Authority, or the Declaration, dated Aug. 2, 2018, PCT/US2017/065188, 13 pages, ISA/KR.

*Primary Examiner* — Catherine Loikith
(74) *Attorney, Agent, or Firm* — Haynes and Boone, LLP

(57) ABSTRACT

A method includes directing a wellbore fluid into a flow control assembly coupled to a completion string positioned within a wellbore, the flow control assembly including at least a first fluidic device defining a flow passage, where the flow passage is formed of a material having a known wettability selected to correspond to a component of the wellbore fluid. The pressure change along the flow passage is measured and utilized to determine fluid cut based on a predetermined correspondence between pressure change and component cut for the first fluidic device. Multiple fluidic devices, each selected to have a wettability responsive to a different component of the wellbore fluid, may be aligned in parallel or series to determine the cut of multiple components in the fluid.

21 Claims, 8 Drawing Sheets

(51) Int. Cl.
*E21B 49/08* (2006.01)
*G01N 33/28* (2006.01)
*E21B 43/12* (2006.01)

(56) References Cited

U.S. PATENT DOCUMENTS

| | | |
|---|---|---|
| 8,739,886 B2 | 6/2014 | Fripp et al. |
| 9,133,685 B2 * | 9/2015 | Fripp .................... E21B 43/32 |
| 2007/0062695 A1 | 3/2007 | Harrison et al. |
| 2009/0166037 A1 | 7/2009 | Sroka |
| 2011/0146975 A1 | 6/2011 | O'Malley et al. |
| 2013/0255960 A1 | 10/2013 | Fripp et al. |
| 2015/0021019 A1 | 1/2015 | Veit |
| 2015/0275622 A1 | 10/2015 | Lopez et al. |
| 2019/0120048 A1 * | 4/2019 | Coffin .................... E21B 47/07 |

* cited by examiner

USING FLUIDIC DEVICES TO ESTIMATE CUT OF WELLBORE FLUIDS

CROSS REFERENCE TO RELATED APPLICATIONS

The present application is a U.S. National Stage patent application of International Patent Application No. PCT/US2017/065188, filed on Dec. 7, 2017, the benefit of which is claimed and the disclosure of which is incorporated herein by reference in its entirety.

BACKGROUND

In management of fluids associated with hydrocarbon wells, it is often beneficial to know the percentage or "cut" of one or more components of a flow steam. Knowledge of the cut of a flow stream may be useful in regulating the flow stream, particularly as the flow stream relates to the production of fluids from a wellbore. A variety of reasons or purposes can necessitate such regulation, including, for example, prevention of water and/or gas coning, minimizing water and/or gas production, minimizing sand production, maximizing oil production, balancing production from various subterranean zones, equalizing pressure among various subterranean zones, and/or the like.

A number of fluidic devices or modules are available for regulating the flow of formation fluids. Some of these devices are non-discriminating for different types of formation fluids and can simply function as a "gatekeeper" for regulating access to the interior of a wellbore pipe, such as a well string. Such gatekeeper devices can be simple on/off valves or they can be metered to regulate fluid flow over a continuum of flow rates. Other types of devices for regulating the flow of formation fluids can achieve at least some degree of discrimination between different types of formation fluids. Such devices can include, for example, tubular flow restrictors, nozzle-type flow restrictors, autonomous inflow control devices (AICD), non-autonomous inflow control devices, ports, tortuous paths, combinations thereof, and the like. Based on the cut, the foregoing fluidic devices or modules may be adjusted to alter flow rates in order to achieve desired results. For example, when it is determined that a production interval is producing more of one type of fluid than other fluids, a well operator may then decide to reduce or cease production from that production interval, which will result in more efficient production operations for the well.

Because cut is such an important measurement in the control of wellbore fluids, a number of technologies have been developed to measure fluid composition, particularly with respect to oil-and-water mixtures. These technologies include Coriolis densitometers, microwave analyzers, infrared spectrometers and capacitive analyzers, among others. One drawback to such technologies is the difficulty of implementing such downhole.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure relates to downhole fluid flow regulation and, more particularly, to estimating water cut (or alternatively oil fraction) in a producing interval using fluidic devices and fluid sensors.

The embodiments discussed herein describe the use of a plurality of fluidic devices arranged in a flow control assembly of a downhole completion to estimate the fluid cut in a subterranean production fluid. While the embodiments may be described in terms of cut estimates with respect to water, oil and gas, the embodiments may be applicable to the measurement of the cut of any fluid in a stream. The fluidic devices exhibit different but known flow resistances to fluids having known fluid properties (e.g., viscosity, density, etc.). The cut or percentage of a fluid component within a flow stream can be estimated based on the pressure drop of the flow stream passing through a fluidic device having a wettability selected to correspond with the particular fluid component. In particular, the fluidic device has a flow passage or path formed of or otherwise lined with a material having a known wettability selected to correspond with one component of the flow stream. A fluid cut can be estimated by measuring the pressure drop of the flow stream through the fluidic device. Thus, a water cut of a flow steam may then be estimated based on the flow conditions measured as the flow stream passes through a water-wettable or hydrophilic fluidic device. Likewise, an oil cut of a flow steam may then be estimated based on the flow conditions measured as the flow stream passes through an oil-wettable or oleophilic fluidic device. The principles of the present disclosure may also be employed in estimating the gas cut in a fluid.

Figure 1:
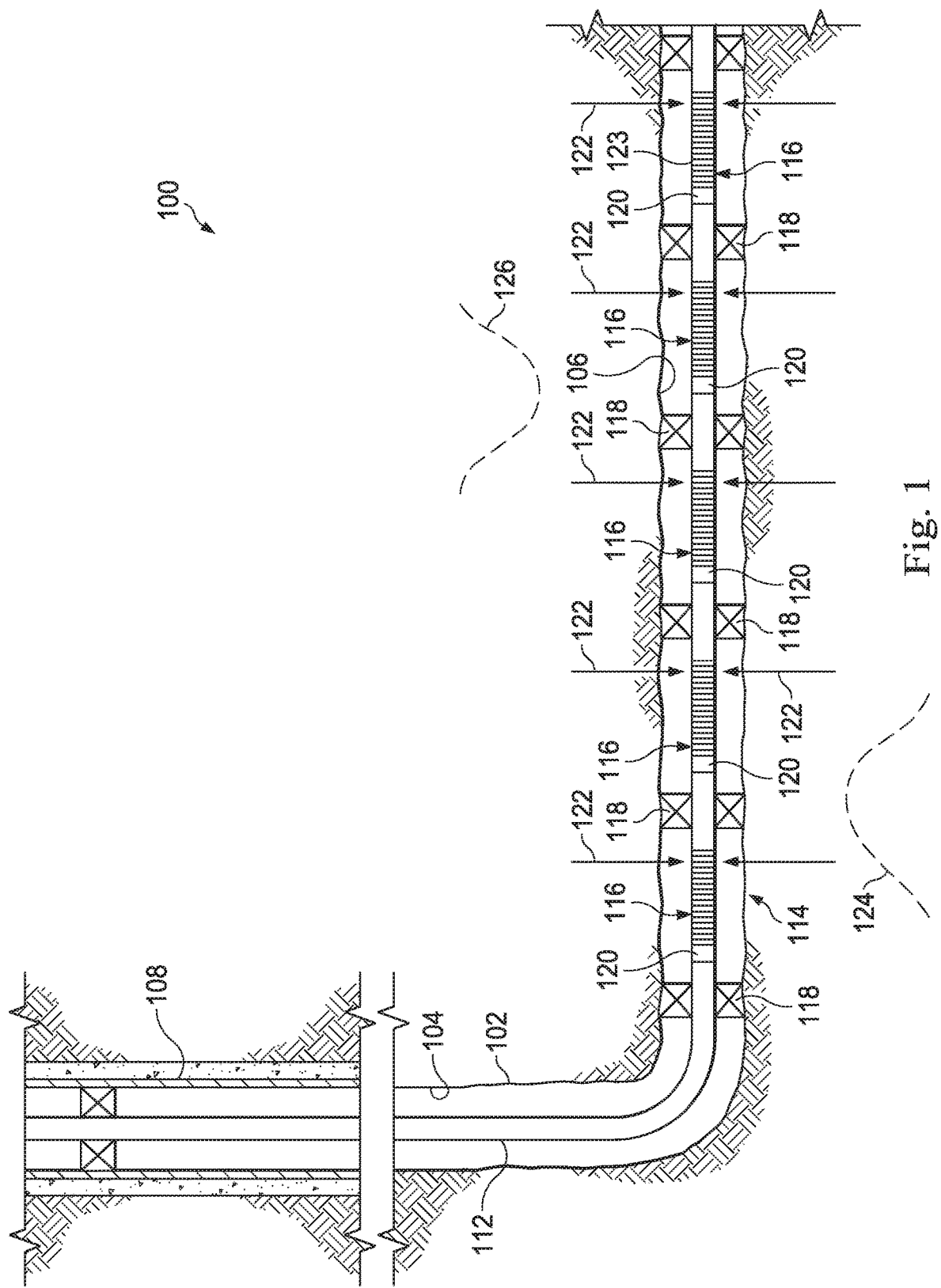
FIG. 1 is a schematic diagram of an exemplary well system that may employ one or more of the principles of the present disclosure.

FIG. 1 is a schematic diagram of an exemplary well system 100 that may employ one or more of the principles of the present disclosure, according to one or more embodiments. As depicted, the well system 100 includes a wellbore 102 that extends through various earth strata and has a substantially vertical section 104 that transitions into a deviated or substantially horizontal section 106, where the deviated section 106 may extend through a hydrocarbon bearing subterranean formation 110. Portions of vertical section 104 and deviated section 106 may have a string of casing 108 cemented therein. In some embodiments, the deviated section 106 may be uncompleted and otherwise characterized as an "open hole" section of the wellbore 102. In other embodiments, however, the casing 108 may extend into the deviated section 106.

A string of production tubing 112 may be positioned within the wellbore 102 and extend from a surface location (not shown), such as the Earth's surface. The production tubing 112 provides a conduit for fluids extracted from the formation 110 to travel to the surface location for production. A completion string 114 may be coupled to or otherwise form part of the lower end of the production tubing 112 and arranged within the wellbore 102, such as in deviated section 106. The completion string 114 divides the wellbore 102 into various production intervals adjacent the subterranean formation 110. To accomplish this, as depicted, the completion string 114 may include a plurality of flow control assemblies 116 axially spaced apart from one another along portions of the production tubing 112. Each flow control assembly 116 may be positioned between a pair of wellbore packers 118 that provides a fluid seal between the completion string 114 and the inner wall of the wellbore 102, and thereby defining discrete production intervals. One or more of the flow control assemblies 116 may further include at least one fluidic device 120 used to convey or otherwise regulate the flow of fluids 122 (i.e., a production fluid stream) into the completion string 114 and, therefore, into the production tubing 112.

In operation, each flow control assembly 116 serves the primary function of filtering particulate matter out of the fluids 122 originating from the formation 110 such that particulates and other fines are not produced to the surface. The fluidic devices 120 then operate to regulate the flow of the fluids 122 into the completion string 114. Regulating the flow of fluids 122 in each production interval may be advantageous in preventing water coning 124 or gas coning 126 in the subterranean formation 110. Other uses for flow regulation of the fluids 122 include, but are not limited to, balancing production from multiple production intervals, minimizing production of undesired fluids, maximizing production of desired fluids, etc.

In the illustrated embodiment, each flow control assembly 116 may include one or more filter media 123 that serve to filter the incoming fluids 122. In the illustrated embodiment, filter media 123 are sand screens, however, such sand screens may be replaced with any other type of filter media, such as a slotted liner or the like, without departing from the scope of the disclosure. In yet other embodiments, the filter media may be omitted from one or more of the flow control assemblies 116 and the incoming fluids 122 may instead be conveyed directly to the fluidic devices 120 without filtration. Accordingly, use of filter media in FIG. 1 is for illustrative purposes only and should not be considered limiting to the present disclosure.

It should be noted that even though FIG. 1 depicts the flow control assemblies 116 as being arranged in an open hole portion of the wellbore 102, embodiments are contemplated herein where one or more of the flow control assemblies 116 is arranged within cased portions of the wellbore 102. Also, even though FIG. 1 depicts a single flow control assembly 116 arranged in each production interval, any number of flow control assemblies 116 may be deployed within a particular production interval without departing from the scope of the disclosure. In addition, even though FIG. 1 depicts multiple production intervals separated by the packers 118, any number of production intervals with a corresponding number of packers 118 may be used. In other embodiments, the packers 118 may be entirely omitted from the completion interval, without departing from the scope of the disclosure.

Furthermore, while FIG. 1 depicts the flow control assemblies 116 as being arranged in the deviated section 106 of the wellbore 102, the flow control assemblies 116 are equally well suited for use in the vertical section 104 or portions of the wellbore 102 that are deviated, slanted, multilateral, or any combination thereof. Moreover, while FIG. 1 generally depicts a land-based drilling assembly, those skilled in the art will readily recognize that the principles described herein are equally applicable to subsea operations that employ floating or sea-based platforms and rigs, without departing from the scope of the disclosure. The use of directional terms such as above, below, upper, lower, upward, downward, left, right, uphole, downhole and the like are used in relation to the illustrative embodiments as they are depicted in the figures, the upward direction being toward the top of the corresponding figure and the downward direction being toward the bottom of the corresponding figure, the uphole direction being toward the surface of the well and the downhole direction being toward the toe of the well.

Figure 2:
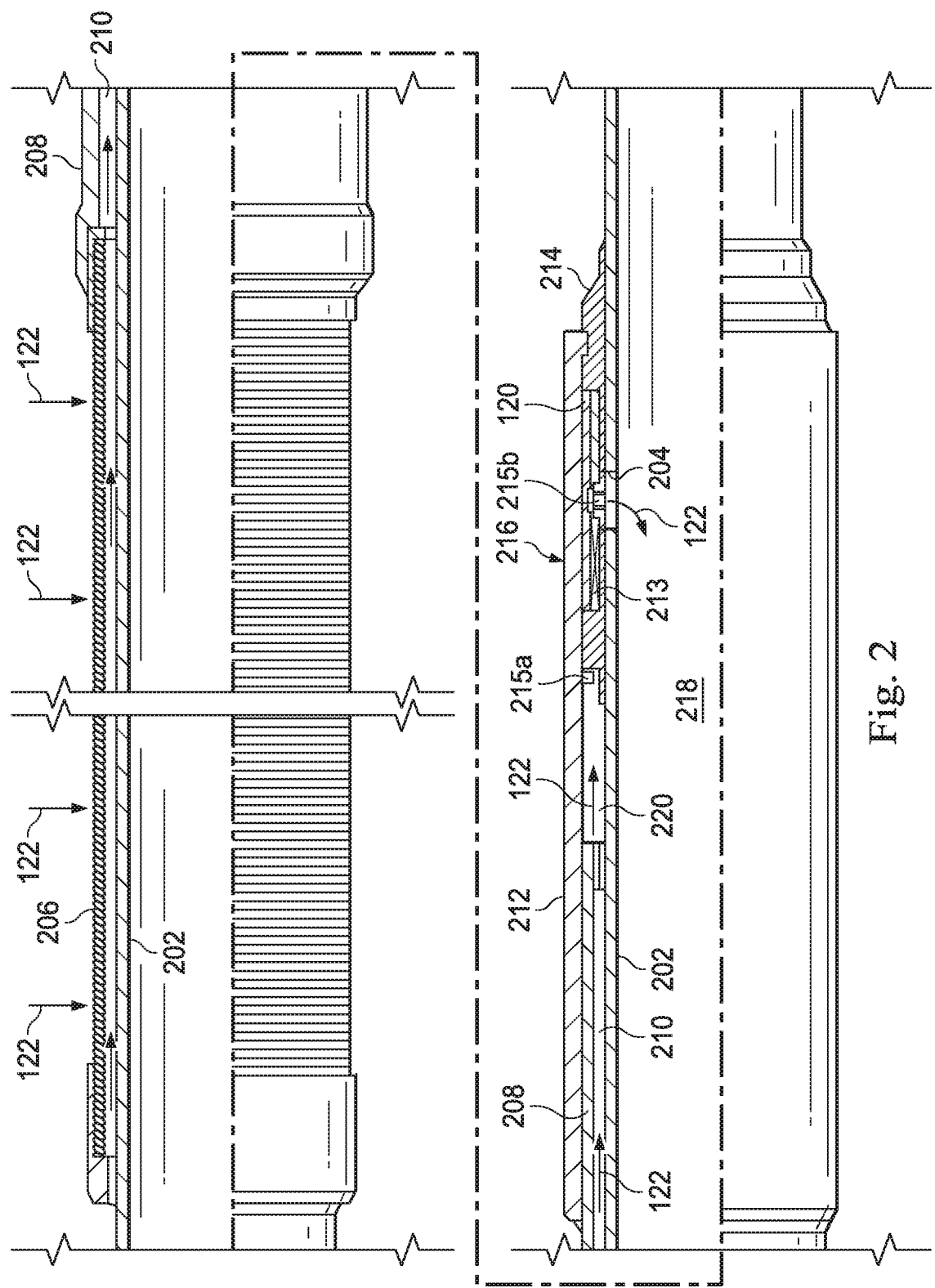
FIG. 2 is a partial cross-sectional view of successive axial sections of an example flow control assembly.

FIG. 2 is a partial cross-sectional view of successive axial sections of an example flow control assembly 116, according to one or more embodiments. The flow control assembly 116 may be any of the flow control assemblies 116 shown in FIG. 1. As illustrated, the flow control assembly 116 includes a base pipe 202 that defines one or more production ports 204. The base pipe 202 forms part of the completion string 114 (FIG. 1) and otherwise fluidly communicates with the production tubing 112 (FIG. 1). A filter media 206 is positioned around (about) an uphole portion of the base pipe 202. As illustrated, the filter media 206 comprises a screen element, such as a wire wrap screen, a woven wire mesh screen, a prepacked screen or the like, but could alternatively comprise a slotted pipe. The filter media 206 is designed to allow fluids to flow therethrough but prevent particulate matter of a predetermined size from flowing therethrough. As indicated above, however, the filter media 206 may alternatively be omitted from the flow control assembly 116.

Positioned downhole of the filter medium 206 is a screen interface housing 208 that forms an annulus 210 jointly with the base pipe 202. A flow control shroud 212 is secured to the downhole end of the screen interface housing 208. At its downhole end, the flow control shroud 212 is securably connected to a support assembly 214, which is secured to base pipe 202. The various connections of the components of the flow control assembly 116 may be made in any suitable fashion including welding, threading, and the like, as well as through the use of various mechanical fasteners, such as bolts, screws, pins, snap rings, etc.

Positioned between the support assembly 214 and the flow control shroud 212 are a plurality of fluidic devices, generally depicted at reference numeral 120. The fluidic devices 120 may be alternately referred to as "fluidic modules," or "fluidic components." In some embodiments, the fluidic devices 120 may be configured to convey incoming fluids into the base pipe 202 via the flow port(s) 204. In other embodiments, however, the one or more of the fluidic devices 120 may be configured to regulate or control the flow of incoming fluids. In such embodiments, the fluidic devices 120 may comprise, for example, inflow control devices (ICD) or autonomous inflow control devices (AICD). An ICD is designed to exhibit a viscosity dependent fluid flow resistance in the form of a positive flowrate response to decreasing fluid viscosity. In contrast, an AICD is designed to exhibit a viscosity dependent fluid flow resistance in the form of a negative flowrate response to decreasing fluid viscosity. Flow changes through the ICD and/or the AICD can be a function of density, wettability, and flow rate, in addition to viscosity. In some embodiments, the same ICD or AICD may exhibit a positive and a negative flowrate response depending on the flow regime. More particularly, a given ICD or AICD may exhibit a negative flow rate response for one combination of viscosity, wettability, flow rate, and density, but may exhibit a positive flow rate response for a different combination of viscosity, flow rate, and density, without departing from the scope of the disclosure.

Regardless of the type of fluidic device 120 utilized, in all embodiments, the fluidic devices include a flow passage 213 a portion of which is formed of or otherwise lined with a material having a known wettability selected to correspond with an anticipated component of fluid 122. The cut of the component of fluid 122 then can be estimated by measuring the pressure drop of the flow stream passing through fluidic device 120. Thus, in the illustrated embodiment, a first pressure sensor 215a is positioned upstream of a portion of the flow passage 213 and a second pressure sensor 215b is positioned downstream of the first pressure sensor 215b in order to measure the pressure drop of fluid 122 as it comes into contact with the wettable material. Thus, for example, fluidic device 120 may be a "water-wettable" or hydrophilic fluidic device if flow passage 213 is formed of or lined with a hydrophilic or "water wettable" material, while fluidic device 120 may be an "oil-wettable" or oleophilic fluidic device if flow passage 213 is formed of or lined with an oil wettable material or otherwise by a hydrophobic material.

Hydrophobic materials, i.e., those materials tending to repel or fail to mix with water, may include silica/polyaniline (PAni), alkanes, silica, silicone, and fluorocarbon. In other embodiments, such hydrophobic materials may comprise nanoparticles, such as an agglomeration of alumina nanoparticles that are coated with carboxylic acid or a coating of copper nanoparticles. In other embodiments, such hydrophobic material is a ceramic such as a ceramic comprising a lanthanide oxide. In yet other embodiments, polymers may be used as the hydrophobic material, such as such as acrylics, carbonates, amides and imides, olefins, etc.

Hydrophilic materials, i.e., those materials having a tendency to mix with, dissolve in, or be wetted by water, include silane coupling agents (silane can also be hydrophobic). In other embodiments, silicone can be modified to contain hydrophilic groups, such as with an increase in the alkylene oxide content and utilized to form or otherwise line a portion of flow passage 213. Likewise, siloxanes are hydrophilic and may be utilized. Further, many polymers and polymer oxide surfaces are hydrophilic, such as polyethyenimine, polyacrylamide, polyethers, and may be used in other embodiments.

In other embodiments, rather than, or in conjunction with a portion of flow passage 213 formed of or lined with a material of a known wettability, a portion of the flow passage may include an interactive surface which surface interacts with distinct fluids differently, resulting in pressure changes that can be utilized to estimate fluid cut. For example, the interactive surface may be textured, such as with micro-grooves, micro-slots, micro-pores, or micro-openings that may be sized to interact differently with different fluid components, resulting in different pressure responses based on the presence or absence of a particular component in fluid stream 122. In yet other embodiments, the interactive surface may be formed of a particle bed employing gravel, conglomerate, or other particulates; a mesh, such as a weave, braid, knit, link, or fabric; a filter; a membrane; or a narrow tube. The interactive surface may naturally exhibit wettability behavior as described above. In other embodiments, the interactive surface may be coated hydrophilic, oleophilic fluidic or hydrophobic material to enhance or to create the desired wettability behavior.

In one or more embodiments, the interactive surface may be positioned parallel or perpendicular to the major axis of flow passage 213. For example, in some embodiments, a perforated grate or screen may be posited along flow passage 213 perpendicular to the direction of flow. Additionally, the grate or screen may be coated with a material having a select wettability or, alternatively, or in addition, may support particles selected to have a desired wettability.

It will be appreciated by persons of ordinary skill in the art that the material having a known wettability and the interactive surface displaying known wettability behavior may thus be utilized as described above to estimate fluid cut based on pressure changes in fluid 122 as it flows along passage 213. Moreover, in certain embodiments, the material having a known wettability and/or interactive surface displaying known wettability behavior may be used in conjunction with other fluidic devices, such as those fluidic device known as fluidic diodes having fluid circuits (discussed below with respect to FIG. 3 and FIG. 4).

Although the disclosure is not limited to use of the foregoing fluidic devices 120 in completion strings, but may be utilized to measure cut in conjunction with any fluid flow structure, fluidic devices 120 have been found to be particularly effective in estimating the cut of fluid 122 flowing into completion flow control assemblies 116. Thus, as shown in FIG. 2, the fluidic devices 120 may be positioned about the circumference of the base pipe 202 within a flow control section 216 in a variety of configurations. In some embodiments, for example, two or more of the fluidic devices 120 may be arranged in parallel within the flow control section 216. In other embodiments, or in addition thereto, two or more of the fluidic devices 120 may be arranged in series within the flow control section 216, without departing from the scope of the disclosure. Moreover, the fluidic devices 120 may be circumferentially distributed at uniform or non-uniform intervals about the periphery of the base pipe 202. Where two or more fluidic devices 120 are utilized, each fluidic devices 120 may be selected to exhibit different wettability characteristics in response to the presence of a particular component in a fluid stream 122.

The fluidic devices 120 are fluidly coupled to and otherwise in fluid communication with the production port(s) 204. During the production phase of well operations, the fluid 122 is drawn into the flow control assembly 116 from a surrounding formation (i.e., the formation 110 of FIG. 1). After being filtered by the filter medium 206, if present, the fluid 122 flows into the annulus 210, which communicates with an annular region 220 defined between the base pipe 202 and the flow control shroud 212. The fluid 122 then circulates into the fluidic device 120 where the pressure of the fluid 122 is measured upstream and downstream of the wettable portion of flow passage 213 utilizing pressure sensors 215a and 215b, respectively. The fluidic devices 120 then expel the fluid 122 toward the production port(s) 204 to be discharged into the central flow passage 218 for production to the well surface.

Figure 3A:
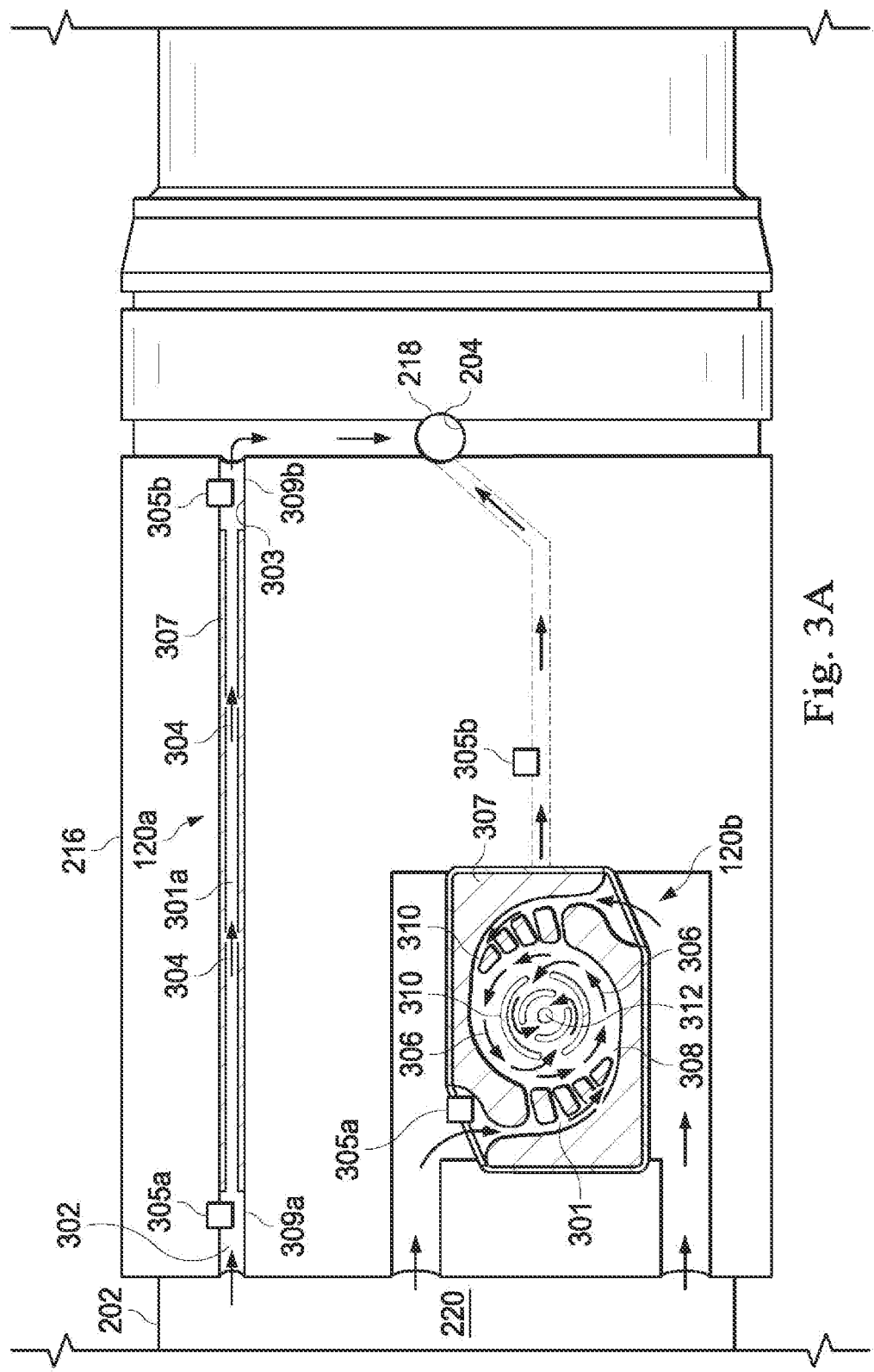
FIG. 3A is a schematic view of an example embodiment of the flow control section of FIG. 2.

FIG. 3A is a schematic view of an example embodiment of the flow control section 216 of FIG. 2, according to one or more embodiments. The flow control shroud 212 (FIG. 2) has been removed in FIG. 3A to enable viewing of the fluidic devices included in the fluid circuit of the flow control section 216. The fluidic devices are depicted as a first fluidic device 120a and a second fluidic device 120b arranged in parallel and in fluid communication with the production port(s) 204 (only one shown).

The first fluidic device 120a is depicted as an inflow control device (ICD) that simply forms a flow passage 301a for fluid flow therethrough, as indicated by arrows 304. More specifically, the first fluidic device 120a is depicted in the form of a flow tube 302 having an internal surface 303.

In one or more embodiments, a portion of the internal surface 303 is formed of or coated with a material 307 of a select wettability. Thus, for example, to the extent first fluidic device 120a is used to measure water cut, internal surface 303 may be coated with a hydrophilic material 307. As a fluid enters the flow tube 302, first pressure device 305a measures a first fluid pressure. As the fluid exits flow tube 302, second pressure device 305b measures a second fluid pressure. The presence of water cut will impact the pressure differential between the first and second fluid pressures measured by the first and second pressure devices 305a, 305b, respectively. Thus, the presence of a large water cut will result in a larger pressure differential because of the hydrophilic material 307 along flow passage 301a, it being understood that as the fluid flows across the internal surface 303 coated with a hydrophilic material 307, water within the fluid will bind to the internal surface, causing an increase in the pressure differential. Conversely, the presence of very little or a smaller water cut will result in a small pressure differential between first and second fluid pressures. The more water in the fluid flow, the more "binding" and the greater the pressure differential measured by sensors 305a and 305b. While first fluidic device 120a is depicted as an inflow control device selected to control fluid flow into base pipe 202, it will be appreciated that first fluidic device 120a may be any device along which a flow passage 301a is defined, a portion of which is formed of or otherwise lined with a material having a known wettability selected to correspond with an anticipated component of fluid 122. Thus, while a relatively narrow flow tube 302 is depicted, flow tube 302 may have a larger diameter or be a flow channel or duct so long as it is formed of or otherwise lined with a material 307 having a known wettability. Likewise, as evidenced below, while some embodiments of flow tube 302 and flow passage 301a are linear extending from a first end 309a to a second end 309b, in other embodiments, flow passage 301 may be curvilinear.

The second fluidic device 120b is depicted as an autonomous inflow control device (AICD) that provides resistance to fluid flow therethrough, as indicated by arrows 306. More specifically, the second fluidic device 120b is depicted in the form of a fluid diode having a vortex chamber 308 in which one or more fluid guides 310 are provided. The second fluidic device 120b is sometimes referred to as a "vortex chamber diode." In the case of a relatively high viscosity fluid composition containing predominately oil, flow through the second fluidic device 120b may progress relatively unimpeded. On the other hand, in the case of a relatively low viscosity fluid composition containing predominately water, the fluids entering the vortex chamber 308 will travel primarily in a tangentially direction and will spiral around the vortex chamber 308 with the aid of the fluid guides 310 before eventually exiting through a centrally-located outlet 312. In other embodiments, the fluid circulating through the vortex chamber 308 may be rotated and translated on a helical passage and still generally function the same.

In the case of second fluidic device 120b, the flow passage 301b spirals about outlet 312. All or a portion of the flow passage 301b may be formed of or otherwise lined with a material 307. For example, fluid guides 310 may be formed of wettability material 307. As a fluid enters the vortex chamber 308, first pressure device 305a measures a first fluid pressure. As the fluid exits vortex chamber 308, second pressure device 305b measures a second fluid pressure. The presence of water cut will impact the pressure differential between the first and second fluid pressures measured by the first and second pressure devices 305a, 305b, respectively. Of course, it will be appreciated that in the case of fluid spiraling around the vortex chamber 308, the tangential velocity of the fluid flow 306 produces centrifugal force that impedes radial flow. Consequently, spiraling fluids passing through the second fluidic device 120b encounter significant resistance. However, the second fluidic device 120b will still exhibit a pressure response based on the presence of fluid cut selected to correspond to the wettability material 307 along flow passage 301b.

In the depicted configuration, the first fluidic device 120a and the second fluidic device 120b are arranged in parallel in the fluid circuit defined in the flow control section 216. The first and second fluidic devices 120a, b share a common fluid source from the annular region 220, and a common fluid discharge into the central flow passage 218 via the production port(s) 204. In this configuration, the first and second fluidic devices 120a, b exhibit a common upstream fluid pressure as measured by pressure sensors 305a, but may have differing fluid pressures at the respective down stream pressure sensors 305b.

As the cut of a particular component in a fluid stream increases, wettable materials selected to have high wettability in the presence of the component will have a greater effect on the flow stream, resulting in a corresponding increase in pressure between the two pressure sensors.

Figure 3B:
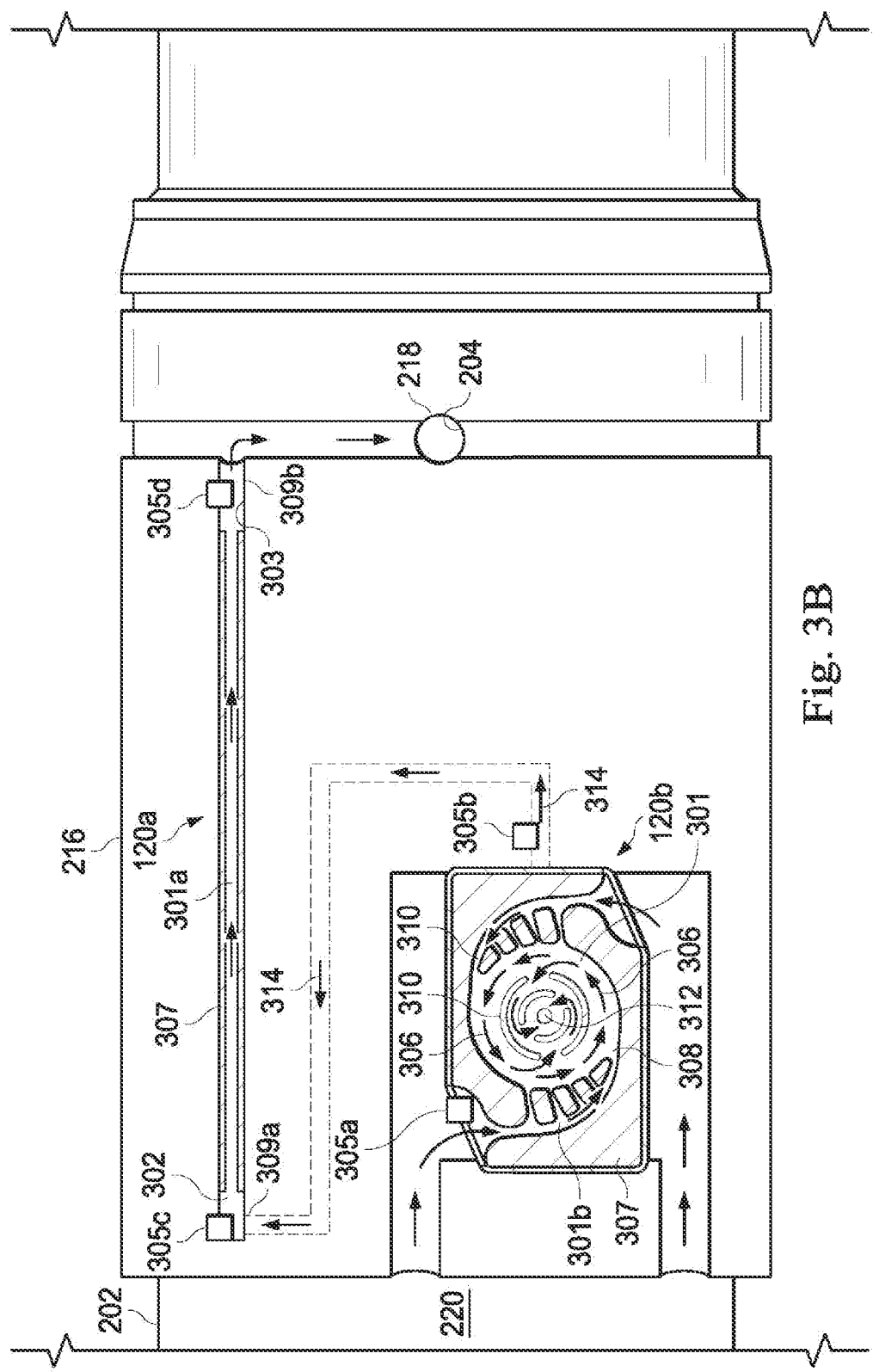
FIG. 3B is a schematic view of another example embodiment of the flow control section of FIG. 2.

FIG. 3B is a schematic view of another example embodiment of the flow control section 216 of FIG. 2, according to one or more additional embodiments. The flow control shroud 212 (FIG. 2) has again been removed in FIG. 3B to enable viewing of the fluid circuit provided in the flow control section 216. Similar to the embodiment of FIG. 3A, the fluidic devices are again depicted as the first fluidic device 120a and the second fluidic device 120b, where the first fluidic device 120a may comprise an ICD in the form of the flow tube 302, and the second fluidic device 120b may comprise an AICD in the form of a fluid diode having the vortex chamber 308, the fluid guides 310, and the centrally-located outlet 312.

Unlike the embodiment of FIG. 3A, however, the first and second fluidic devices 120a, b of FIG. 3B are arranged in series in the flow control section 216. The fluid flowing through the first and second fluidic devices 120a, b originates from the annular region 220 and circulates first through the second fluidic device 120b. Upon exiting the second fluidic device 120b at the outlet 312, the fluid then flows to the first fluidic device 120a, as shown by the arrows 314. The fluid then circulates through the first fluidic device 120a before being discharged into the central flow passage 218 via the production port(s) 204 following the first fluidic device 120a. In certain embodiment, second fluidic device 120b is utilized to control fluid flow into base pipe 202, while first fluidic device 120a may be utilized to measure a component cut of a fluid exiting the second fluidic device 120b. Alternatively, each fluidic device 120a, 120b may have a different wettability material 307 incorporated therein, and thus, each fluidic device 120a, 120b may be used to measure a different component cut of the fluid flowing there through. For example, fluidic device 120a may have a wettability material 307 employed therewith that is hydrophilic, while fluidic device 120b may have a wettability material 307 employed therewith that is oleophilic, such that the cut of each of water and oil may be estimated. Of course, the foregoing arrangement may also be utilized where the first and second fluidic devices 120a, 120b are arranged in parallel (such as in FIG. 3A) as opposed to series. In FIG. 3B, a first pressure sensor 305a is disposed adjacent the inlet or otherwise upstream of fluidic device 120b, a second pressure sensor 305b is disposed adjacent the outlet or otherwise downstream of fluidic device 120b. In other embodiments, pressure sensors 305a, b may be located at a spaced apart interval along flow passage 301b. A third pressure sensor 305c is disposed adjacent the inlet or otherwise upstream of fluidic device 120a, a fourth pressure sensor 305d is disposed adjacent the outlet or otherwise downstream of fluidic device 120a. In other embodiments, pressure sensors 305c, d may be located at a spaced apart interval along flow passage 301a.

According to embodiments of the present disclosure, the fluidic devices 120a, b arranged within the flow control section 216 may be used to help estimate the water cut or alternatively the oil fraction in a producing completion (e.g., the completion string 114). As used herein, the term "water cut" refers to the ratio of water produced in an incoming fluid stream from a surrounding subterranean formation as compared to the volume of total liquids produced. Alternatively, the "water cut" could refer to the ratio of water produced in an incoming fluid stream from a surrounding subterranean formation as compared to the mass of total liquids produced. The term "water cut" could also refer to a fraction of the total flow that comprises water. As used herein, the term "oil fraction" refers to the fraction of oil contained in the total liquids produced, less the fraction corresponding to the water cut. The fluidic devices 120a, b exhibit different responses to fluids having suspected fluid components depending on the wettable material utilized in each fluidic device. Consequently, the water cut of the fluid can be estimated by employing a water wettable material along a flow passage and measuring the change in fluid pressure along the flow passage. While the foregoing has been described in terms of water or oil cut in a fluid, it will be appreciated, however, that the principles of the present disclosure may also be used to estimate the gas content in an incoming fluid stream from a surrounding subterranean formation, referred to herein as the "gas cut" of the flow, or for the cut of other components that might be present in a fluid stream.

As will be appreciated, knowing the water cut (or gas cut) in a produced fluid may prove advantageous in allowing a well operator to intelligently produce fluids by limiting the production of certain types of fluids (e.g., water), and maximizing the production of other fluids (e.g., oil). More specifically, the flow control assemblies 116 may form part of an intelligent completion having one or more interval control valves that are actuatable choke or expose the production port(s) 204. Once it is determined that the water cut in a produced stream of fluid surpasses a predetermined limit, the well operator may selectively actuate the interval control valve through a specific flow control assembly 116 to choke or cease production from that production interval. This may prove advantageous in providing more efficient production operations for the well, and may also provide information used to model the reservoir and thereby increase the ultimate recovery of the formation.

FIGS. 4A-4F are cross-sectional side views of a variety of example fluidic devices that may be employed in accordance with the principles of the present disclosure. Even though the fluidic devices 120a,b of FIGS. 3A and 3B have been depicted and described as having particular designs and configurations, the fluidic devices 120a,b used to help determine (estimate) water cut may alternatively exhibit a variety of alternate designs without departing from the scope of the present disclosure. FIGS. 4A-4F, for example, depict fluidic devices 400a through 400f, respectively, that may be employed in accordance with the principles of the present disclosure. Accordingly, the fluidic devices 120a,b of FIGS. 3A-3B may be replaced with any of the fluidic devices 400a-f.

Figure 4A:
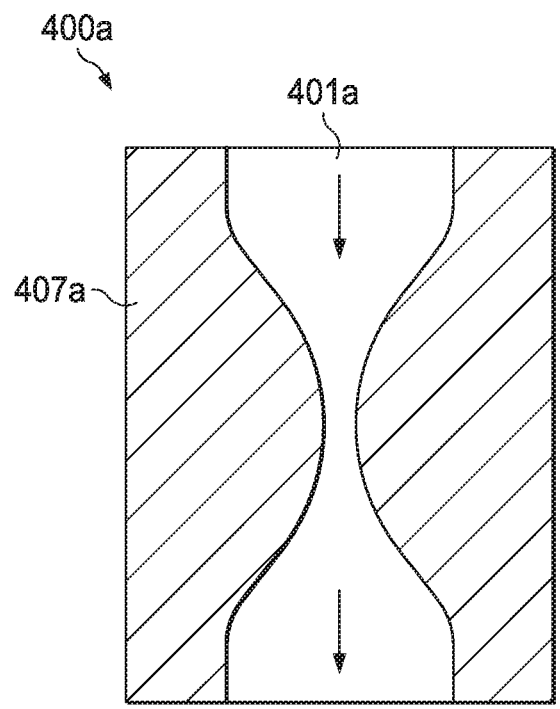
FIGS. 4A-4F are cross-sectional side views of a variety of example fluidic devices that may be employed in accordance with the principles of the present disclosure.
Figure 4B:
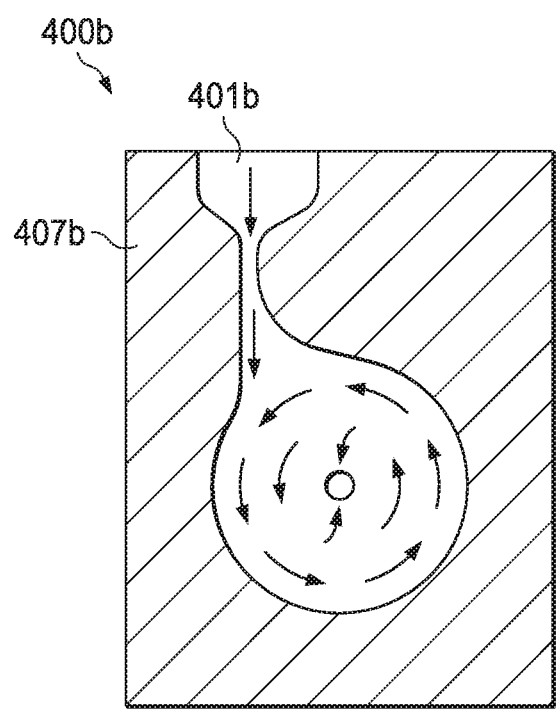
Figure 4C:
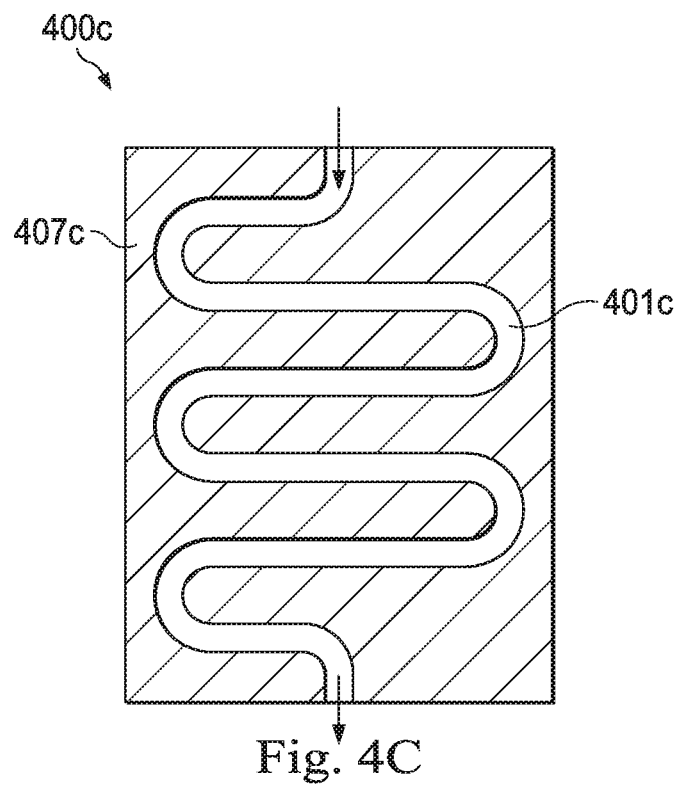
Figure 4D:
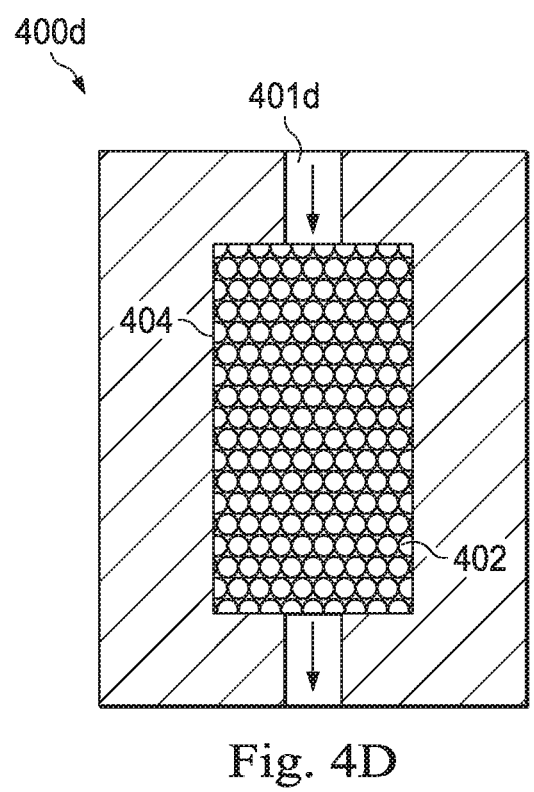
Figure 4E:
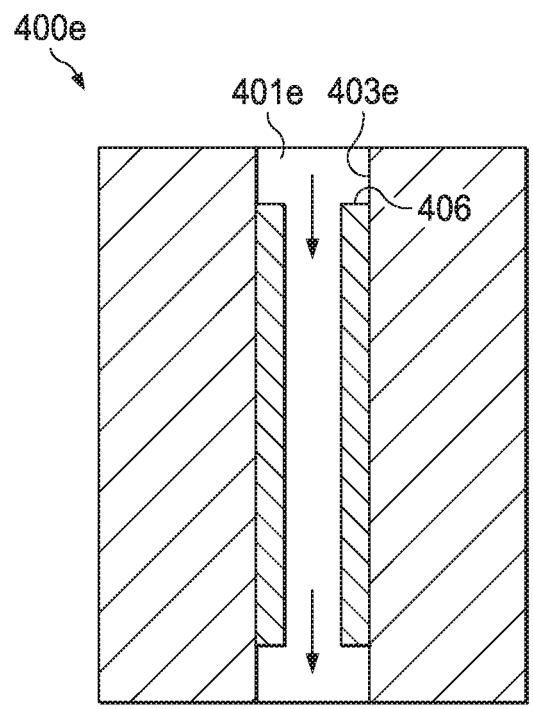
Figure 4F:
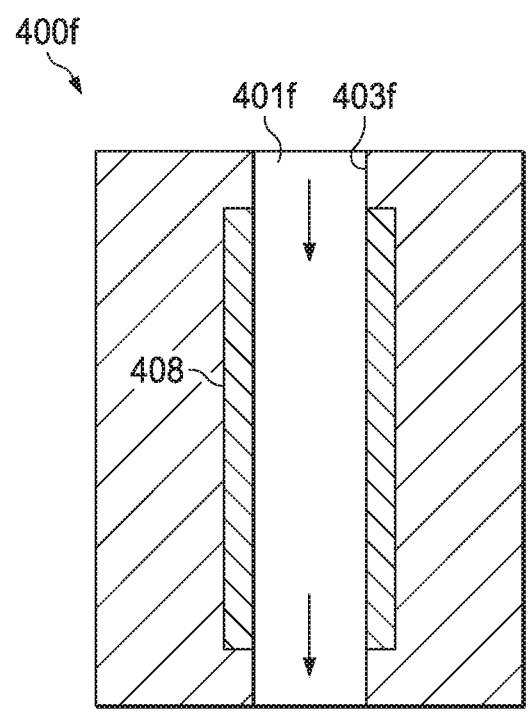

In FIG. 4A, the fluidic device 400a is depicted generally as a nozzle. As shown, fluidic device 400a defines a flow passage 401a and is formed of a wettable material 407a selected to have a known wettability and exhibit know wettability responses in the presence of a fluid component corresponding to the wettable material 407a. In FIG. 4B, the fluidic device 400b comprises a vortex chamber diode similar in some respects to the fluidic device 120b of FIGS. 3A-3B. As shown, fluidic device 400b defines a flow passage 401b and is formed of a wettable material 407b selected to have a known wettability and exhibit know wettability responses in the presence of a fluid component corresponding to the wettable material 407b. In FIG. 4C, the fluidic device 400c comprises a flow tube that provides a tortuous passage flow. As shown, fluidic device 400c defines a flow passage 401c and is formed of a wettable material 407c selected to have a known wettability and exhibit know wettability responses in the presence of a fluid component corresponding to the wettable material 407c. In FIG. 4D, the fluidic device 400d comprises a wettable material 402 disposed within a chamber 404. In the illustrated embodiment, the wettable material 402 is porous and may be, for example, beads, coated gravel, conglomerate, open-celled foam, membrane, particulates or other filler material having a select wettability. In this regard, the wettable material 402 may be deployed as a particle bed through which the fluid stream along flow passage 401d passes. In FIG. 4E, the fluidic device 400e comprises a flow channel 406, similar in some respects to the fluidic device 120a of FIGS. 3A-3B. As shown, fluidic device 400e defines a flow passage 401e and is characterized by an inner surface 403e coated with a wettable material 406 selected to have a known wettability and exhibit know wettability responses in the presence of a fluid component corresponding to the wettable material 406. In FIG. 4F, the fluidic device 400f defines a flow passage 401f and is characterized by an inner surface 403f having a wettable material 408 in the form of an interactive surface which surface interacts with distinct fluids differently, resulting in pressure changes that can be utilized to estimate fluid cut. For example, the interactive surface may be textured, such as with micro-grooves, micro-slots, micro-pores, or micro-openings that may be sized to interact differently with different fluid components, resulting in different pressure responses based on the presence or absence of a particular fluid component in fluid stream. In yet other embodiments, the interactive surface may be formed of a particle bed employing a mesh, such as a weave, braid, knit, link, fabric or membrane. The interactive surface may naturally exhibit wettability behavior as described above.

It should be noted that although the fluidic devices 400a-f are depicted as two-dimensional shapes, one or more of the fluidic devices 400a-f could exhibit a height or depth variation. For example, the vortex chamber diode of the fluidic device 400b of FIG. 4B could be conically shaped. Moreover, while not shown, one or more of the fluidic devices 400a-f may provide and otherwise include moving parts, without departing from the scope of the disclosure.

Figure 5:
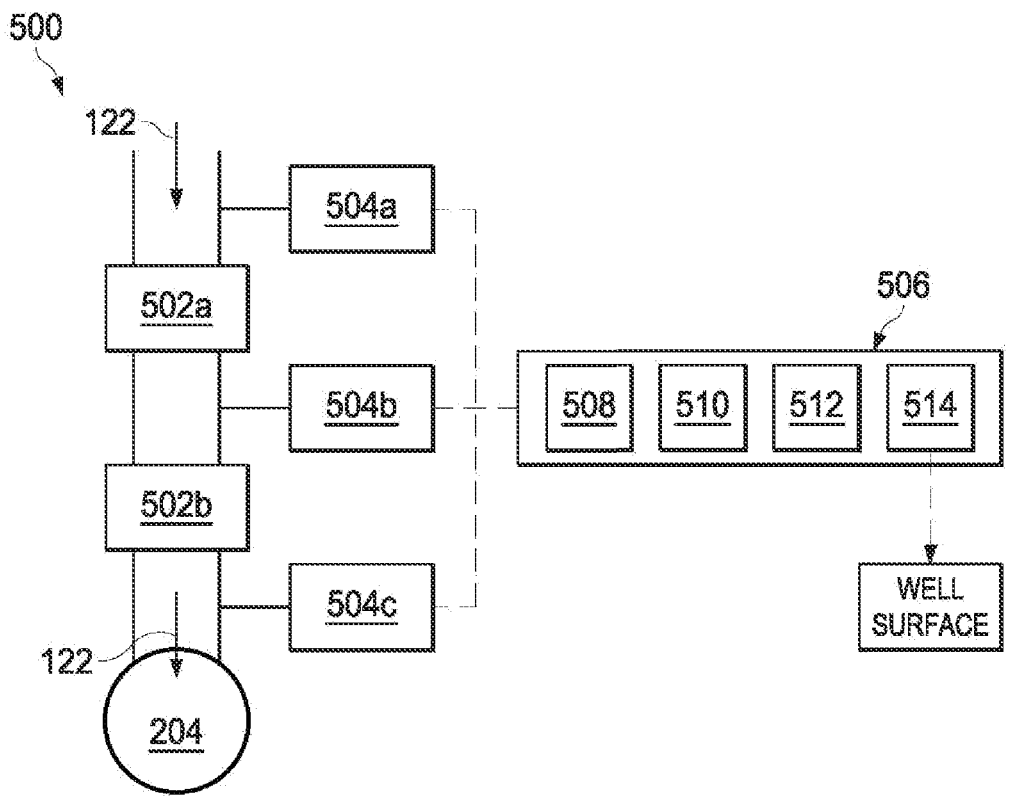
FIG. 5 is a schematic diagram of an example fluid circuit.

FIG. 5 is a schematic diagram of an example fluid circuit 500 used to help determine water cut (or alternatively the gas cut), according to one or more embodiments of the present disclosure. The fluid circuit 500 may be provided or otherwise defined within the flow control section 216 (FIGS. 2 and 3A-3B) of the flow control assembly 116 (FIG. 2).

Accordingly, the fluid circuit 500 generally depicts the flow passage for the fluid 122 originating, for example, from the subterranean formation 110 (FIG. 1), and the fluid circuit 500 may regulate the flow to the production port(s) 204 to be discharged into the central flow passage 218 (FIGS. 2 and 3A-3B). In some applications, the fluid 122 circulating through the fluid circuit 500 includes at least two fluidic constituents of water and oil. In other applications, however, the fluid 122 circulating through the fluid circuit 500 might only include a single fluidic component or phase of pure water or pure oil, for example or pure gas. In such applications, the fluid circuit 500 will nonetheless be able to measure the fluid 122 and indicate that the fluid 122 is pure.

The fluid 122 circulates through at least two fluidic devices arranged in series in the fluid circuit 500 and shown as a first fluidic device 502a and a second fluidic device 502b. The fluidic devices 502a,b may be the same as or similar to any of the fluidic devices mentioned herein, including the fluidic devices 120a,b of FIGS. 3A-3B and the fluidic devices 400a-400f of FIGS. 4A-4F. The first and second fluidic devices 502a,b, however, are different from each other and thereby exhibit different flow characteristics. In some embodiments, for instance, one may be an ICD and the other an AICD, although each may be an ICD or an AICD or other fluidic device, without departing from the scope of the disclosure. The fluidic devices 502a,b will exhibit a different response to the flow of water, oil, and/or gas. This difference can be achieved by changes in the wettability material associated with each fluidic device 502a, 502b. For example, the two fluidic devices 502a, b could both be tubes or channels similar to the fluidic device 400e of FIG. 4E, but each coated with a different wettable material 406.

As illustrated, the fluid circuit 500 may include a plurality of pressure sensors, shown as a first pressure sensor 504a, a second pressure sensor 504b, and a third pressure sensor 504c. The first pressure sensor 504a is communicably coupled to the fluid circuit 500 upstream of the first fluidic device 502a and configured to measure and otherwise detect a pressure of the fluid 122 at that location. The second pressure sensor 504b is communicably coupled to the fluid circuit 500 between the first and second fluidic devices 502a,b (i.e., downstream from the first fluidic device 502a and upstream from the second fluidic device 502b), and configured to measure and otherwise detect the pressure of the fluid 122 at that location. Lastly, the third pressure sensor 504c is communicably coupled to the fluid circuit 500 downstream of the second fluidic device 502b and configured to measure and otherwise detect the pressure of the fluid 122 at that location.

In some embodiments, for instance, each pressure sensor 504a-c may comprise a pressure transducer configured to measure the pressure of the fluid 122 at the corresponding locations in the fluid circuit 500.

Each of the pressure sensors 504a-c may be communicably coupled (either wired or wirelessly) to a computer system 506 configured to monitor pressure conditions in the fluid circuit 500. The computer system 506 may be located downhole, such as being included in the flow control assembly 116 (FIG. 2), or may alternatively be located at the well surface. The computer system 506 may include, for example, computer hardware and/or software used to operate the pressure sensors 504a-c. The computer hardware may include a processor 508 configured to execute one or more sequences of instructions, programming stances, or code stored on a non-transitory, computer-readable medium (e.g., a memory) and can include, for example, a general purpose microprocessor, a microcontroller, a digital signal processor, or any like suitable device.

The computer system 506 may also include a library or database 510 that stores known wettability and pressure response data for the fluidic devices 502a, b based on the wettable material employed therein. Such data may include design and flow characteristics of each fluidic device 502a,b. As discussed below, this operational data may be accessed by the processor 508 during operation to compare the real-time data obtained by the fluid sensors 504a-c and thereby determine or otherwise estimate the water cut percentage of the fluid 122 based on the wettability response of the fluidic devices 502a, b.

In some embodiments, the computer system 506 may further include a power source 512 that provides electrical power to the fluid sensors 504a-c for operation. The power source 512 may comprise, but is not limited to, one or more batteries, a fuel cell, a nuclear-based generator, a flow induced vibration power harvester, or any combination thereof.

In embodiments where the computer system 506 is located downhole, the computer system 506 may further include a bi-directional communications module 514 to enable transfer of data and/or control signals to/from the computer system 506 and a well surface location. Accordingly, the communications module 514 may be communicably coupled (either wired or wirelessly) to the well surface location to enable transfer of data or control signals to/from the well surface location during operation. The communications module 514 may include one or more transmitters and receivers, for example, to facilitate bi-directional communication with the surface location. As a result, a well operator at the well surface may be apprised of the real-time water cut percentage of the fluid circuit 500, and may be able to send command signals to the flow control assembly 116 (FIG. 2) to adjust and otherwise regulate the flow of the fluid 122 when desired.

In example operation, the pressure sensors 504a-c may each comprise differential pressure transducers that increase the resolution of any obtained measurements. The first and second pressure sensors 504a,b detect the pressure of the fluid 122 before and after the first fluidic device 502a, respectively, and the third fluid sensor 504c detects the pressure of the fluid 122 following the second fluidic device 502b.

Each pressure sensor 504a-c communicates its respective readings (measurements) to the computer system 506 (located downhole or at the well surface), which calculates a pressure differential across the first and second fluidic devices 502a,b. More specifically, the computer system 506 calculates a first pressure drop ($\Delta P_1$) across the first fluidic device 502a and a second pressure drop ($\Delta P_2$) across the second fluidic device 502b. The computer system 506 may then calculate the estimate water cut of fluid 122 based on the pressure differential $\Delta P$ whereby the greater the pressure differential, the greater the water cut or percentage of water within the fluid 122.

Referring again to FIG. 5, in some embodiments, the computer system 506 may estimate (determine) the water cut (or alternatively the oil or gas cut) for the fluid 122, as generally described above. More specifically, the first pressure drop $\Delta P_1$ across the first fluidic device 502a or the second pressure drop $\Delta P_2$ across the second fluidic device 502b may be used to estimate the fluid cut. In short, for each fluidic device, a pressure drop across a flow passage having a particular wettable material disposed along it can be correlated to a particular fluid cut reactive to the wettable material. In certain embodiments, the correlation may be determined by utilizing a lookup table generated through experimental data acquired for a particular fluidic device. For example, a fluid containing components of water and oil may be passed through a fluidic device that is water wettable or hydrophilic. The fluid may utilize known water percentages or cuts, such as 100%, 75%, 50% and 0%, and the pressure change across the fluidic device due to the presence of water can be recorded in a look up table, thereby permitting correlation between the pressure drop and water cut for the particular fluidic device under consideration. This process can be repeated for any type of fluidic device and for any fluid component for which the fluidic device is wettable. In other embodiments, a theoretical correlation can be calculated based on physical characteristics and dimensions of the fluidic device being utilized.

Figure 6:
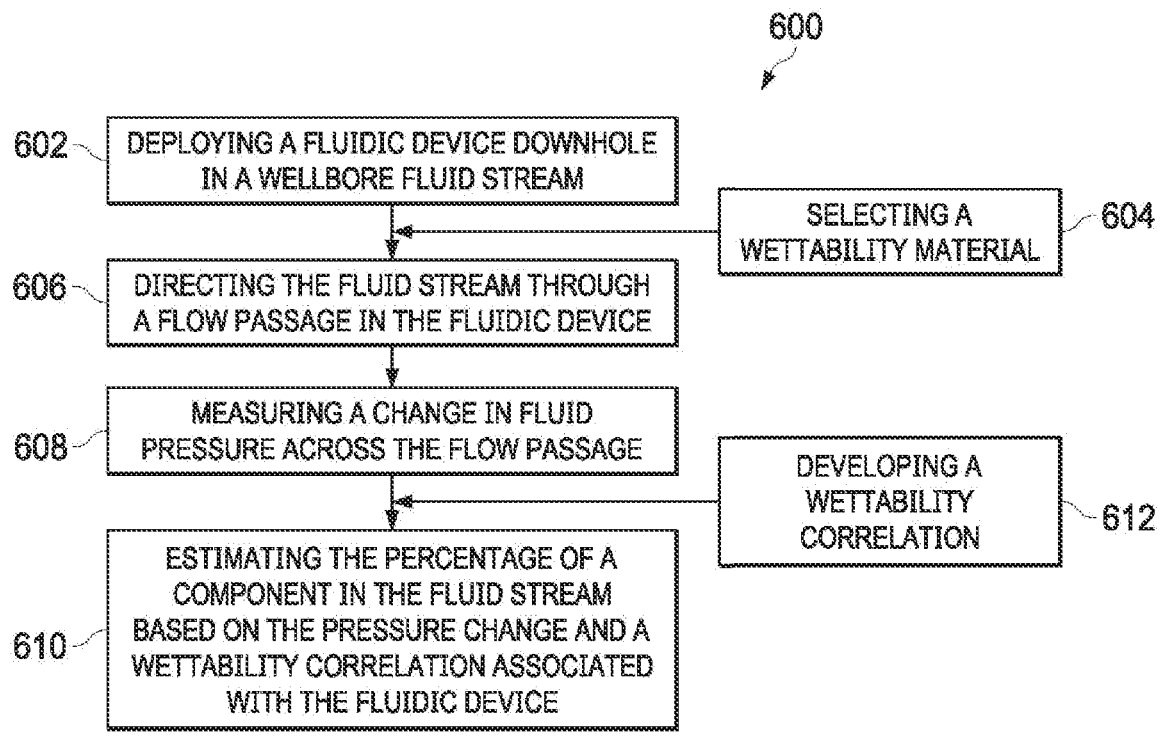
FIG. 6 is a flow chart of a method for determining component cut of a downhole fluid.

With reference to FIG. 6, a method 600 for determining the percentage of a component present in a dowhole fluid is illustrated. In a first step 602, a fluidic device, such as fluidic devices 120, 400 and 502 described above, is deployed in a wellbore fluid stream. The fluidic devices include a flow passage for the downhole fluid. In some embodiments, the fluidic devices are deployed downhole in a wellbore, while in other embodiments, the fluidic devices may be deployed anywhere along a fluid flow stream for fluids flowing into or out of a wellbore. In some embodiments, the fluidic device may be incorporated into a completion string, such as the completion strings described herein, while in other embodiments, the fluidic device may be incorporated in another downhole tool, including, without limitation, drilling tools or production tools. In the case of completion string, the fluidic devices may be inflow control devices (ICD) or autonomous inflow control devices (AICD), such as fluidic diodes. In some embodiments, the fluidic device may simply be a linear flow tube while in other embodiments, the fluidic device may have a curvilinear circuit. In instances where it is desirable to determine the percentage of different components in a fluid stream, multiple fluidic devices may be deployed, where each fluidic device is utilized to identify the percentage of a different component in the fluid stream. For example, a first fluidic device may be utilized to identify the percentage of water present in a fluid stream and a second fluidic device may be utilized to identify the percentage of oil present in a fluid stream. These fluidic devices may be deployed in series, so that a fluid stream flows first through the first fluidic device and then through the second fluidic device. In other embodiments, the fluidic devices may be deployed in parallel, where different portions of the fluid stream flows through each fluidic device at the same time. Of course, in other embodiments, the multiple fluidic devices may be disposed to react to the same component, in such case, providing redundancy in percentage estimations.

As illustrated in step 604, the fluidic device is specifically selected based on its reaction in response to the presence of a particular fluid component in a fluid stream. The reaction of the fluidic device can be utilized to predict the percentage of the component in the fluid stream. Along at least a portion of the flow passage is a wettable material or interactive surface having physical characteristics that result in known, predictable wettability behavior in the presence of a particular fluid component. In this regard, as stated above, the fluidic device is specifically selected to be wettable with respect to a particular fluid, such as for example, water, oil or a gas. Thus, the flow passage is lined with, coated with or otherwise formed of a wettable material or interactive surface that corresponds to the particular fluid component the fluidic device is being utilized to estimate. In this regard, the wettable material may be hydrophobic material, which in some embodiments may include silica/polyaniline (PAni), alkanes, silica, silicone, fluorocarbon, alumina nanoparticles coated with carboxylic acid, copper nanoparticles, lanthanide oxide, acrylics, carbonates, amides and imides or olefins. Likewise, the wettable material may be hydrophilic material, which in some embodiments may include silane, siloxanes, polyethyenimine, polyacrylamide or polyethers. The interactive surface may include various physical features or construction that lend themselves to exhibit wettability behavior. For example, the physical features may include micro-grooves, micro-slots, micro-pores, micro-openings, open-celled foam, woven, braided, knitted, or linked fabric or mesh; or a particle bed employing gravel, conglomerate, or other particulates. In one embodiment, the wettable material is an open-celled foam comprising polytetrafluoroethylene.

In step 606, at least a portion of the fluid stream is directed or caused to flow along the flow passage within the fluidic device. The flow passage may be linear or curvilinear. In some embodiments, the flow passage may be characterized by one or more physical dimensions, such as a length (L) and a diameter (D). In the case of multiple fluidic devices, the fluid stream may be directed serially first the one fluidic device and then through the other fluidic device. Alternatively, in the case of parallel fluidic devices, a portion of the fluid stream may be directed through one fluidic device and a different portion of the fluid stream may be directed through the other fluidic device.

In step 608, the pressure change of the fluid stream along at least a portion of the flow passage is determined. In one or more embodiments, a first pressure may be determined by a first pressure sensor positioned adjacent or upstream of the inlet to the fluidic device and a second pressure may be determined by a pressure sensor downstream or adjacent the outlet to the fluidic device. Utilizing the two pressure measurements, a change in pressure can be determined.

In step 610, the percentage of a component in the fluid stream is estimated based on the determined pressure change. Specifically, for a flow passage with a wettability selected for a particular component, as the percentage of the particular component in a fluid stream increases, the pressure of the fluid stream increases because a greater amount of the component is adhering to the surfaces along the flow passage. In contrast, if a flow passage is wettable with respect to a particular component and that component is not present in the fluid steam, then very little change in the fluid pressure would expect to be observed arising from adhesion of any component of the fluid stream to a surface along the flow passage. The percentage of the component in the fluid stream may be specifically determined by referencing a wettability correlation in which the a pressure change is correlated to the percentage of the component in the fluid stream.

As illustrated by step 612, in some embodiments, one step in the method 600 for determining the percentage of a component present in a dowhole fluid may include establishing a wettability correlation for a particular fluidic device. It will be appreciated that each distinct fluidic device may have a wettability response based on the physical design of the fluidic device, including the wettability material or the interactive surface deployed along or otherwise forming the flow passage. In one or more embodiments, the wettability correlation for a fluidic device may be determined empirically. Specifically, employing a fluidic device having a wettability selected to correspond to a select component, such as water or oil, a fluid stream having a first known percentage of the select component is passed through the flow passage of the select fluidic device and a fluid pressure change across the flow passage is recorded. Thereafter, the percentage of the select component in the fluid stream is altered to a second known percentage and the fluid stream is again passed through the flow passage of the select fluidic device. Again, the fluid pressure change across the flow passage is recorded along with the percentage of the component in the fluid stream. This step may be repeated as necessary to develop the wettability correlation in the form of a "lookup" table, linear or curvilinear plot of the relationship between the pressure change and the percentage of the component in the fluid stream. The wettability correlation data may be stored on computer memory storage for subsequent reference during deployment of the specific fluidic device. In other embodiments, the wettability correlation may be developed theoretically by correlating the physical dimensions of a fluidic device, the material of known wettability deployed along the flow passage of the device and a pressure change across the flow passage. For example, a wettability correlation may be expressed in the form of $$L \cdot W \cdot \% = \Delta P,$$

where L represents physical dimensions of the fluidic device, such as length, diameter, etc.; W represents the wettability of the fluidic device with respect to a particular component of a fluid stream; % represents the percentage of the particular component in a fluid stream; and $\Delta P$ represents the change in pressure due to the presence of the particular component in the fluid stream.

Thus an oilfield tubular string has been described. Embodiments of the tubular string may include a base pipe that defines a central flow passage and one or more flow ports; a flow control assembly coupled to the base pipe and including a first fluidic device and a second fluidic device, where the first fluidic device has a first flow passage having a first wettability and the second fluidic device has a second flow passage having a second wettability different from the wettability of the first fluidic device; a first pressure sensor disposed at a first end of the first flow passage and a second pressure sensor disposed at a second end of the first flow passage; a third pressure sensor disposed at a second end of the second flow passage; a wettability correlation between a fluid pressure change across the first flow passage and wettability of the first flow passage; a wettability correlation between a fluid pressure change across the second flow passage and wettability of the second flow passage; and a computer system communicably coupled to the pressure sensors and programmed to estimate a percentage of a component in a fluid stream based on the measured pressure changes across the fluidic devices and the wettability correlation for each fluidic device. Other embodiments include a tubular that defines a flow passage and one or more flow ports; a flow control assembly coupled to the tubular and including a first fluidic device and a second fluidic device, where the first fluidic device has a first flow passage having a first wettability and the second fluidic device has a second flow passage having a second wettability different from the wettability of the first fluidic device; a first pressure sensor disposed at a first end of the first flow passage and a second pressure sensor disposed at a second end of the first flow passage; a third pressure sensor disposed at a second end of the second flow passage; a wettability correlation between a fluid pressure change across the first flow passage and wettability of the first flow passage; a wettability correlation between a fluid pressure change across the second flow passage and wettability of the second flow passage; and a computer system communicably coupled to the pressure sensors and programmed to estimate a percentage of a component in a fluid stream based on the measured pressure changes across the fluidic devices and the wettability correlation for each fluidic device. Other embodiments include a tubular that defines a flow passage and one or more flow ports; a first fluidic device and a second fluidic device, where the first fluidic device has a first flow passage having a first wettability and the second fluidic device has a second flow passage having a second wettability different from the wettability of the first fluidic device; a first pressure sensor disposed at a first end of the first flow passage and a second pressure sensor disposed at a second end of the first flow passage; a third pressure sensor disposed at a second end of the second flow passage; a wettability correlation between a fluid pressure change across the first flow passage and wettability of the first flow passage; a wettability correlation between a fluid pressure change across the second flow passage and wettability of the second flow passage; and a computer system communicably coupled to the pressure sensors and programmed to estimate a percentage of a component in a fluid stream based on the measured pressure changes across the fluidic devices and the wettability correlation for each fluidic device.

For any of the foregoing embodiments, the downhole tool may further include any one of the following elements, alone or in combination with each other:

The wettability correlation between a pressure drop across the first flow passage and wettability of the first flow passage comprises at least two different pressure changes, each pressure change associated with a different percentage of a component in a fluid.

The first fluidic device comprises a first flow tube and the second fluidic device comprises a second flow tube, wherein the first flow tube is formed of a hydrophobic material and the second flow tube is formed of an oleophilic material.

The first and second fluidic devices are arranged in series.

The first and second fluidic devices are arranged in parallel.

The first fluidic device and a second fluidic device comprise a flow control assembly.

The tubular is a base pipe that defines a central flow passage.

The tubular comprises a completion string.

The tubular comprises a completion string having a flow control assembly and a production screen.

The first fluidic device comprises a first flow tube and the second fluidic device comprises a second flow tube, wherein the first flow tube is formed of a hydrophobic material and the second flow tube is formed of a hydrophilic material.

The hydrophobic material is selected from the group consisting of silica/polyaniline (PAni), alkanes, silica, silicone, fluorocarbon, alumina nanoparticles coated with carboxylic acid, copper nanoparticles, lanthanide oxide, acrylics, carbonates, amides and imides and olefins.

Hydrophilic material is selected from the group consisting of silane, siloxanes, polyethyenimine, polyacrylamide and polyethers.

A portion of one of the flow passages includes an interactive surface displaying known wettability behavior.

The interactive surface is textured by the formation of features selected from the group consisting of micro-grooves, micro-slots, micro-pores, open-cell foam, and micro-openings.

The interactive surface is coated with a hydrophilic material.

The interactive surface is coated with a hydrophobic material.

The interactive surface comprises a particle bed comprising a particulate selected from the group consisting of gravel, conglomerates, particles coated with a hydrophilic material, particles coated with a hydrophobic material, and particles coated with an oleophilic material. The first fluidic device comprises a first flow tube and the second fluidic device comprises a second flow tube, wherein the first flow tube is formed of a wettable material and the second flow tube is formed of an interactive surface displaying known wettability behavior.

The computer system includes a database that stores known wettability correlation data for the first and second fluidic devices, and wherein the computer system is further programmed to compare the pressure change across a fluidic device against the known wettability correlation data.

The open-celled foam comprises polytetrafluoroethylene.

Thus methods for estimating the percentage of a component in a wellbore fluid stream have been described. Embodiments of the method include deploying a fluidic device downhole in a wellbore fluid stream, the fluidic device having a flow passage formed of a material of known wettability with respect to a select component of a fluid stream; directing the fluid stream through the flow passage; measuring a change in fluid pressure across the flow passage; and estimating the percentage of a component in the fluid stream based on the pressure change and a wettability correlation associated with the fluidic device, the wettability correlation correlating the pressure change in a fluid stream passing through the flow passage of the fluidic device and the percentage of a component within the fluid stream. In other embodiments, the method includes positioning a first fluidic device and a second fluidic device to receive flow from a wellbore into a flow passage of each fluidic device, wherein the flow passage of each fluidic device is formed of a material of known wettability with respect to a select component of a fluid stream; developing a wettability correlation between a pressure change in a fluid stream passing through the flow passage of each fluidic device and the percentage of a component within the fluid stream; directing a fluid stream through the flow passage of each fluidic device; measuring a change in fluid pressure across the flow passage of each fluidic device; and estimating the percentage of a component in the fluid stream based on the pressure change and the wettability correlation associated with each of the first and second fluidic devices. In other embodiments, the method includes selecting a flow passage having a known wettability with respect to a particular liquid; and correlating a plurality of pressure drops across the flow passage with a plurality of percentages of the particular liquid as a component of a fluid stream flowing through the passage. In other embodiments, the method includes selecting a flow passage having a known wettability with respect to a particular liquid; correlating a plurality of pressure drops across the flow passage with a plurality of percentages of the particular liquid as a component of a fluid stream flowing through the passage; positioning the flow passage in a hydrocarbon fluid flow stream having the particular liquid present as a percentage of the flow stream; measuring the pressure change of the fluid flow stream across the flow passage; and utilizing the correlation and the measured pressure change to identify the percentage of the particular liquid in the flow stream.

For any of the foregoing, the methods may further include any one of the following steps, alone or in combination with each other:

Developing a wettability correlation by passing a fluid stream having a first known percentage of a select component through the flow passage of the select fluidic device and recording a fluid pressure change across the flow passage; and altering the passing percentage of the select component in the fluid stream to a second known percentage and passing a fluid stream having the second known percentage of a select component through the flow passage of the select fluidic device and recording a fluid pressure change across the flow passage.

Repeating the step of altering for at least one additional known percentage.

Developing a wettability correlation by correlating the physical dimensions of a fluidic device, the material of known wettability deployed along the flow passage of the device and a pressure change across the flow passage.

Positioning the flow passage in a wellbore.

Positioning the flow passage along a production string deployed dowhole in a wellbore.

Measuring the fluid pressure at spaced apart locations along a flow path through a flow passage.

Deploying a second fluidic device downhole in the wellbore fluid stream, the second fluidic device having a flow passage formed of a material of known wettability with respect to a select component of a fluid stream; directing the fluid stream through the flow passage of the second fluidic device; measuring a change in fluid pressure across the flow passage of the second fluidic device; and estimating the percentage of a component in the fluid stream based on the pressure change and the wettability correlation.

Estimating the percentages of at least two different fluid components in a fluid stream, wherein each fluidic device is wettable for a different fluid component.

One fluidic device is hydrophobic and the other fluidic device is hydrophilic.

The fluid stream is directed serially though the first fluidic device and then the second fluidic device.

A first portion of the fluid stream is directed through the first fluidic device and a second portion of the fluid stream is directed in parallel though the second fluidic device.

The first fluidic device and the second fluidic device are wettable with respect to different components of a fluid stream.

Estimating the percentage of two separate components in the fluid stream based on the pressure change and the wettability correlation associated with each of the first and second fluidic devices.

Developing a wettability correlation comprises correlating the physical dimensions of a fluidic device, the material of known wettability deployed along the flow passage of the device and a pressure change across the flow passage.

Although various embodiments and methodologies have been shown and described, the disclosure is not limited to such embodiments and methodologies and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A method for estimating the percentage proportions of a component fluid components in a wellbore fluid stream, the method comprising:
   determining a first wettability correlation between changes in pressure across flow passages of first and second fluidic devices and a percentage of a first select fluid component in the wellbore fluid stream;
   deploying the first fluidic device downhole in the wellbore fluid stream, the flow passage of the first fluidic device formed of a material of known wettability with respect to the first select fluid component of the wellbore fluid stream;
   deploying the second fluidic device downhole in the wellbore fluid stream;
   directing at least a portion of the wellbore fluid stream through the flow passages of the first and second fluidic devices;
   measuring a change in fluid pressure of the wellbore fluid stream across the flow passage of the first fluidic device;
   measuring a change in fluid pressure of the wellbore fluid stream across the flow passage of the second fluidic device; and
   estimating the percentage of the first select fluid component in the wellbore fluid stream based on the pressure changes measured and the first wettability correlation.

2. The method of claim 1,
   wherein determining the first wettability correlation includes:
   passing a fluid stream having a first known percentage of the first select component through the flow passage of the first fluidic device and recording a fluid pressure change across the flow passage;
   altering the first known percentage of the first select component in the fluid stream to a second known percentage and passing a fluid stream having the second known percentage of the first select component through the flow passage of the first fluidic device and recording a fluid pressure change across the flow passage; and
   correlating the first and second known percentages of the first select component with the fluid pressure changes recorded to determine a relationship between the percentage of the first select component and the fluid pressure change across the flow passage of the first fluidic device.

3. The method of claim 2, further comprising repeating the step of altering for at least one additional known percentage.

4. The method of claim 1, wherein establishing the first wettability correlation includes correlating physical dimensions of the first fluidic device, the material of known wettability with respect to the first select component deployed along the flow passage of the first fluidic device and a pressure change across the flow passage of the first fluidic device.

5. The method of claim 1, wherein the flow passage of the second fluidic device is formed of a material of known wettability with respect to a second select fluid component of the fluid stream.

6. The method of claim 5, further comprising:
   determining a second wettability correlation between changes in pressure across the flow passages of the first and second fluidic devices and a percentage of the second select fluid component in the fluid stream; and
   estimating the percentages of at least the first and second select fluid components in the fluid stream.

7. The method of claim 1, wherein one of the first and second fluidic devices is hydrophobic and another one of the first and second fluidic devices is hydrophilic.

8. A method for estimating a proportion of a fluid component in a wellbore fluid stream, the method comprising:
   positioning a first fluidic device and a second fluidic device to receive flow from a wellbore into a flow passage of each fluidic device, wherein the flow passage of each fluidic device is formed of a material of known wettability with respect to a select component of a fluid stream;
   determining a wettability correlation establishing a relationship between pressure changes in a fluid passing through the flow passage of each fluidic device and a percentage of the select fluid component within the fluid;
   directing the wellbore fluid stream through the flow passage of each fluidic device;
   measuring pressure changes in the wellbore fluid stream across the flow passage of each fluidic device; and
   estimating the percentage of the select fluid component in the wellbore fluid stream based on the pressure changes measured and the wettability correlation associated with each of the first and second fluidic devices.

9. The method of claim 8, wherein the wellbore fluid stream is directed serially though the first fluidic device and then the second fluidic device.

10. The method of claim 8, wherein a first portion of the wellbore fluid stream is directed through the first fluidic device and a second portion of the wellbore fluid stream is directed in parallel though the second fluidic device.

11. The method of claim 8, wherein the first fluidic device and the second fluidic device are wettable with respect to different components of the wellbore fluid stream.

12. The method of claim 11, further comprising estimating percentages of two separate components in the fluid stream based on the pressure changes measured and the wettability correlation associated with each of the first and second fluidic devices.

13. The method of claim 8, wherein developing a wettability correlation comprises correlating physical dimensions of a fluidic device, the material of known wettability deployed along the flow passage of the device and a pressure change across the flow passage.

14. An oilfield tubular string, comprising:
   a base pipe that defines a central flow passage and one or more flow ports;
   a flow control assembly coupled to the base pipe and including a first fluidic device and a second fluidic device, where the first fluidic device has a first flow passage having a first wettability and the second fluidic device has a second flow passage having a second wettability different from the wettability of the first fluidic device;

a first pressure sensor disposed at a first end of the first flow passage and a second pressure sensor disposed at a second end of the first flow passage;

a third pressure sensor disposed at a second end of the second flow passage;

a wettability correlation between a fluid pressure change across the first flow passage and wettability of the first flow passage;

a wettability correlation between a fluid pressure change across the second flow passage and wettability of the second flow passage; and a computer system communicably coupled to the pressure sensors and programmed to estimate a percentage of a component in a fluid stream based on the measured pressure changes across the fluidic devices and the wettability correlation for each fluidic device.

15. The tubular string of claim 14, wherein the wettability correlation between a pressure drop across the first flow passage and wettability of the first flow passage comprises at least two different pressure changes, each pressure change associated with a different percentage of a component in a fluid.

16. The tubular string of claim 14, wherein the first fluidic device comprises a first flow tube and the second fluidic device comprises a second flow tube, wherein the first flow tube is formed of a hydrophobic material and the second flow tube is formed of an oleophilic material.

17. The tubular string of claim 14, wherein the first and second fluidic devices are arranged in series.

18. The tubular string of claim 14, wherein the first and second fluidic devices are arranged in parallel.

19. The tubular string of claim 14, wherein the first fluidic device comprises a first flow tube and the second fluidic device comprises a second flow tube, wherein the first flow tube is formed of a hydrophobic material and the second flow tube is formed of a hydrophilic material.

20. The tubular string of claim 19, wherein the hydrophobic material is selected from the group consisting of silica/polyaniline (PAni), alkanes, silica, silicone, fluorocarbon, alumina nanoparticles coated with carboxylic acid, copper nanoparticles, lanthanide oxide, acrylics, carbonates, amides and imides and olefins and the hydrophilic material is selected from the group consisting of silane, siloxanes, polyethyenimine, polyacrylamide and polyethers.

21. The tubular string of claim 14, wherein a portion of one of the flow passages includes an interactive surface displaying known wettability behavior.

* * * * *